US011963809B2

(12) United States Patent
Van Pinxteren et al.

(10) Patent No.: US 11,963,809 B2
(45) Date of Patent: Apr. 23, 2024

(54) X-RAY IMAGING ARRANGEMENT

(71) Applicant: KONINKLIJKE PHILIPS N.V., Eindhoven (NL)

(72) Inventors: Jeffrey Adrianus Wilhelmus Van Pinxteren, Eindhoven (NL); Robertus Johannes Adrianus Van Loon, Eindhoven (NL); Johannes Petrus Martinus Bernardus Vermeulen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 427 days.

(21) Appl. No.: 17/289,860

(22) PCT Filed: Oct. 30, 2019

(86) PCT No.: PCT/EP2019/079600
§ 371 (c)(1),
(2) Date: Apr. 29, 2021

(87) PCT Pub. No.: WO2020/089272
PCT Pub. Date: May 7, 2020

(65) Prior Publication Data
US 2021/0401390 A1 Dec. 30, 2021

(30) Foreign Application Priority Data
Oct. 30, 2018 (EP) .................... 18203289

(51) Int. Cl.
*A61B 6/00* (2006.01)
(52) U.S. Cl.
CPC .......... *A61B 6/4464* (2013.01); *A61B 6/4452* (2013.01); *A61B 6/4458* (2013.01)
(58) Field of Classification Search
CPC .... A61B 6/4464; A61B 6/4452; A61B 6/4458
See application file for complete search history.

(56) References Cited

U.S. PATENT DOCUMENTS

| 4,435,830 A | 3/1984 | Suzuki |
| 4,501,011 A | 2/1985 | Hauck |
| (Continued) | | |

FOREIGN PATENT DOCUMENTS

| CN | 204909474 U | 12/2015 |
| JP | 9276258 A | 10/1997 |

OTHER PUBLICATIONS

International Search Report and Written Opinion of PCT/EP2019/079600, dated Jan. 20, 2020.
(Continued)

*Primary Examiner* — Chih-Cheng Kao

(57) ABSTRACT

The present invention relates to X-ray imaging. In order to provide a facilitated and space-saving X-ray imaging apparatus, an imaging arrangement (10) for X-ray imaging is provided that comprises a lower movable support arrangement (12) movably holding an X-ray source (14), and an upper movable support arrangement (16) movably holding an X-ray detector (18). The lower movable support arrangement is configured to be mounted to a floor (20), and the upper movable support arrangement is configured to be mounted to a ceiling (22). The lower movable support arrangement comprises a lower boom (24) rotatably attached to a lower base (26). The lower boom comprises two rotatably connected lower arms (28), and the lower base is rotatable around a vertical axis (30). The upper movable support arrangement comprises an upper boom (32) rotatably attached to an upper base (34). The upper boom comprises two rotatably connected upper arms (36). The rotation axes of the lower boom are arranged horizontally, and the rotation axes of the upper boom are arranged vertically.

20 Claims, 9 Drawing Sheets

(56) References Cited

U.S. PATENT DOCUMENTS

| | | | |
|---|---|---|---|
| 4,807,273 A | 2/1989 | Haendle | |
| 4,894,855 A * | 1/1990 | Kresse | B25J 9/0084 |
| | | | 378/189 |
| 5,901,200 A * | 5/1999 | Krause | A61B 6/4441 |
| | | | 378/197 |
| 6,200,024 B1 | 3/2001 | Negrelli | |
| 6,431,751 B1 * | 8/2002 | Everett | A61B 6/4233 |
| | | | 378/197 |
| 6,435,715 B1 | 8/2002 | Betz | |
| 6,733,176 B2 | 5/2004 | Schmitt | |
| 6,872,000 B2 | 3/2005 | Atzinger | |
| 7,018,097 B2 | 3/2006 | Schmitt | |
| 7,832,927 B2 | 11/2010 | Dyreby | |
| 8,459,867 B2 | 6/2013 | Muller | |
| 2003/0091156 A1 | 5/2003 | Crain | |
| 2004/0008820 A1 * | 1/2004 | Schmitt | A61B 6/4441 |
| | | | 378/193 |
| 2008/0037701 A1 | 2/2008 | Banks | |
| 2011/0069818 A1 | 3/2011 | Muller | |
| 2015/0117603 A1 | 4/2015 | Keeve | |
| 2018/0242938 A1 * | 8/2018 | Tanaka | A61B 6/587 |

OTHER PUBLICATIONS

Gaasbeek, R.I. et al "Image-based Estimation and Nonparametric Modeling", University of Technology, 2015, IEEE Conference on Cotnrol and Applications.

Benz, Robyn Melanie et al "Initial Evaluation of image performance of a 3-D X-ray system: Phantom-based comparison of 3-D tomography with conventional computer tomography", Journal of Medicla Imaging, vol. 5, No. 1, 2018.

Tuy, Heang E. "An Inversion Formua for Cone-Beam Reconstruction" Society for Industrial and Applied Mathematics, vol. 43, No. 13, Jun. 1983.

Van Der Maas, Rlck "Advanced Geometric Calibration and Control for Medical X-Ray Systems", 2016.

* cited by examiner

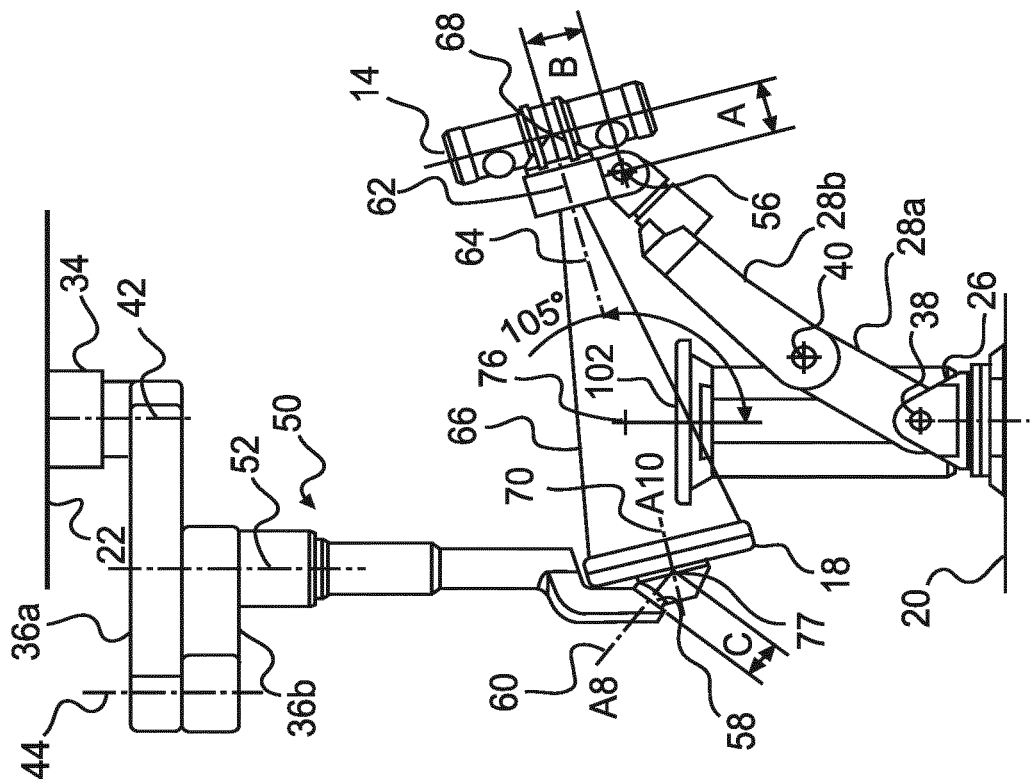
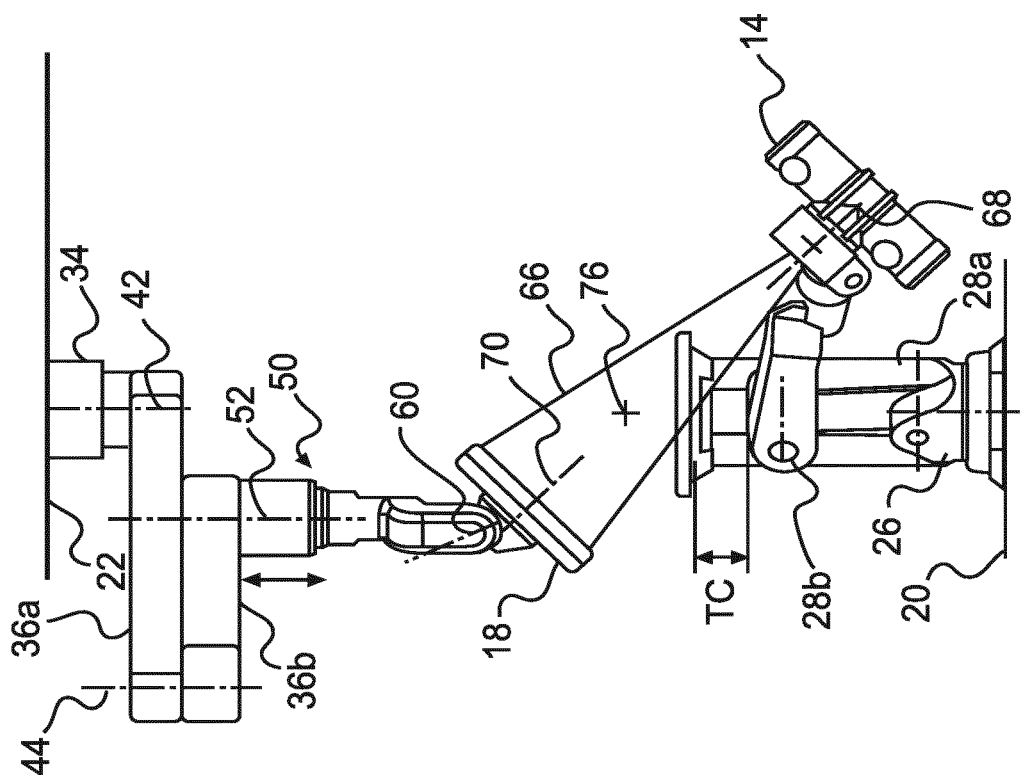

X-RAY IMAGING ARRANGEMENT

CROSS-REFERENCE TO PRIOR APPLICATIONS

This application is the U.S. National Phase application under 35 U.S.C. § 371 of International Application No. PCT/EP2019/079600, filed on Oct. 30, 2019, which claims the benefit of European Patent Application No. 18203289.6, filed on Oct. 30, 2018. These applications are hereby incorporated by reference herein.

FIELD OF THE INVENTION

The present invention relates to X-ray imaging, and relates in particular to an imaging arrangement for X-ray imaging, to an X-ray imaging system and to a method for moving an imaging arrangement for X-ray imaging.

BACKGROUND OF THE INVENTION

Interventional X-ray imaging systems are used to acquire images of anatomical structures, for example of the cardiovascular system. These images may be used to provide a clinician with feedback during a medical procedure. Further, this may enable advanced minimally invasive treatments. For example, a C-arm structure provides an X-ray source and an X-ray detector moving spherically around an isocenter. This may be used for computed tomography. However, a C-arm is relatively bulky. Therefore, X-ray systems are provided that have individual supports for source and detector.

For example, U.S. Pat. No. 4,807,273 A describes a system with two robot arms holding the source and the detector. As a further example, US 2018/0242938 A1 describes an X-ray imaging system with an X-ray source and X-ray detector supported by seven axis vertical multi joint robots. Operations of the robots are controlled such that the X-ray source and detector move about a patient on a spherical shell centering around an isocenter C.

However, in view of an increasing amount of equipment, it has been shown that a growing demand exists for further reducing the space required by the X-ray examination device.

SUMMARY OF THE INVENTION

There may thus be a need to provide facilitated and space-saving medical X-ray imaging.

The object of the present invention is solved by the subject-matter of the independent claims; further embodiments are incorporated in the dependent claims. It should be noted that the following described aspects of the invention apply also for the imaging arrangement for X-ray imaging, for the X-ray imaging system and for the method for moving an imaging arrangement for X-ray imaging.

According to the present invention, an imaging arrangement for X-ray imaging is provided. The arrangement comprises a lower movable support arrangement movably holding an X-ray source. The arrangement also comprises an upper movable support arrangement movably holding an X-ray detector. The lower movable support arrangement is configured to be mounted to a floor, and the upper movable support arrangement is configured to be mounted to a ceiling. The lower movable support arrangement comprises a lower boom rotatably attached to a lower base. The lower boom comprises two rotatably connected lower arms configured to move in a vertical plane, that is in a plane perpendicular to a ceiling or floor, about corresponding rotation axes that are arranged horizontally, that is parallel to a ceiling or floor. The lower base is rotatable around a vertical axis.

The upper movable support arrangement comprises an upper boom rotatably attached to an upper base. Further, the upper boom comprises two rotatably connected upper arms configured to move in a horizontal plane, that is in a plane parallel to a ceiling or floor, about corresponding rotation axes that are arranged vertically, that is perpendicular to a ceiling or floor. Still further, the upper movable support arrangement comprises a telescopic member movably attached to a free end of one of the rotatably connected upper arms, the telescopic member being configured to allow vertical movements of the X-ray detector.

As a result, the space inside the room that is used for the imaging system is reduced to a minimum and room arrangement is facilitated. This in turns also means optimizing the clinical workflow and improving patient access. Furthermore, the kinematic layout allows for increased motion performance of the support systems, which enables improved image quality at a lower X-ray dose.

According to an example, for the two rotatably connected lower arms, the lower boom comprises a first arm movably attached to the lower base around a first axis, and a second arm movably attached to a free end of the first arm around a second axis. Further, for the two rotatably connected upper arms, the upper boom comprises a third arm movably attached to the upper base around a third axis, and a fourth arm movably attached to a free end of the third arm around a fourth axis. Still further, for the rotation axes of the lower boom, the first axis and the second axis are arranged in a horizontal direction substantially parallel to each other; and, for the rotation axes of the upper boom, the third axis and the fourth axis are arranged in a vertical direction substantially parallel to each other.

According to an example, the lower movable support arrangement further comprises a holding segment movably attached to a free end of the second arm rotatable around a fifth axis perpendicular to the first and second axes, and the X-ray source is movably attached to a free end of the holding segment. The upper movable support arrangement further comprises a vertical telescopic member movably attached to a free end of the fourth arm rotatable around a sixth axis parallel to the third and fourth axes, and the X-ray detector is movably attached to a free end of the vertical telescopic member.

According to an example, the fifth axis is inclined in relation to a longitudinal axis of the second arm in a downward direction.

Thus, further spatial arrangement options are provided.

According to an example, the X-ray source is carried by a mounting segment movably mounted to the holding segment rotatable around a seventh axis perpendicular to the fifth axis. The X-ray detector is carried by a mounting member movably mounted to the telescopic member rotatable around an inclined eighth axis.

According to an example, the eighth axis is inclined in relation to the third, fourth and sixth axes.

According to an option, the eighth axis is inclined to the vertical direction by 52.5°. In an example, the inclination angle is provided within a range of 45° to 60°.

According to an example, the X-ray source is attached to the mounting segment rotatable around a ninth axis that is perpendicular to the seventh axis. The ninth axis is collinear to a centerline of an X-ray bundle direction of the X-ray source. A first offset is provided between the seventh axis and the ninth axis. Further, a second offset is provided between the seventh axis and a focal point of the X-ray source.

According to an example, the second arm is longer than the first arm. In addition, or alternatively, the fourth arm is longer than the third arm.

According to an example, the lower base is mounted to the floor rotatable around a vertical axis. The lower base is movably mounted slidable along a floor rail that allows movement along a length of a patient table. Further, provided as an option, a redundant kinematic layout of seven degrees of freedom in total of the lower system is provided that enables system movements to be programmed such that the lower boom operates within the width of the subject support table.

According to the present invention, also an X-ray imaging system is provided. The system comprises an imaging arrangement for X-ray imaging according to one of the preceding examples, and a subject support table. The lower movable support arrangement is arranged below the subject support table.

The term "subject" may also be referred to as individual. The "subject" may further also be referred to as patient, although it is noted that this term does not indicate whether any illness or disease is actually present with the subject.

According to an example, the lower boom remains below the subject support table when the X-ray source is arranged below the subject support table.

According to another example, the upper movable support arrangement is arranged with its upper base displaced longitudinally and/or sidewardly in relation to the subject support table. The displacement is provided in a length direction of the subject support, e.g. a longitudinal extension of the patient table. The sideward displacement is provided in a width direction of the subject support.

According to the present invention, also a method for acquiring X-ray images of a subject is provided. The method comprises the following steps:

a) providing a subject on a subject support table;
b1) positioning an X-ray source with a lower movable support arrangement mounted to a floor below the subject support table, wherein positioning the X-ray source comprises i) moving two rotatably connected lower arms of a lower boom in a vertical plane about corresponding rotation axes being arranged horizontally and ii) rotating a lower base to which the lower arms are attached around a vertical axis;
b2) positioning an X-ray detector with an upper movable support arrangement mounted to a ceiling; wherein positioning the X-ray detector comprises i) moving two rotatably connected upper arms of an upper boom in a horizontal plane about corresponding rotation axes being arranged vertically and ii) moving the X-ray detector vertically by means of a telescopic member that is movably attached to a free end of one of the rotatably connected upper arms; and
c) generating X-ray radiation with the X-ray source and detecting the generated X-ray radiation with the X-ray detector.

According to embodiments of the invention, the imaging arrangement comprises two non-identical mechatronic systems that differ from each other in their kinematic working scheme for providing six degrees of freedom of movement for the X-ray source and the X-ray detector, respectively. Both systems make optimal use of the space available in the operating room. Thus, less obstruction to clinicians and other medical equipment is caused and patient access is improved, as indicated above.

For the upper part of the imaging arrangement, i.e. the detector support, a ceiling mounted, two-link upper arm is provided having two portions each configured to move in the horizontal plane. For example, movements of the upper arm portions are restricted to movements in the horizontal plane. A telescopic member is attached to a free end of one upper arm portion and used for vertical movements. This setup ensures that all moving components operate either above head height (2.10 m), or directly above the detector.

For the lower part of the imaging arrangement, i.e. the source support, a kinematic layout is provided below the patient table that comprises six rotational degrees of freedom, plus optionally an extra redundant translational movement along a rail. A two-link arm is provided for movements in the vertical plane. For example, movements of the upper arm portions are restricted to movements in the horizontal plane. These horizontal movements may be combined with a rotation of the lower base around a vertical axis for covering different positions in relation to the subject to be radiated. The combination of the two link arm and the rotation around a vertical axis enables system movements to be programmed such that the robot arm operates within a relatively limited space.

In an example, wherein the optional translational movement along the rail is implemented, the robot arm may operate within the width of the patient table, that is, movements of the lower part of the imaging arrangement may be restricted within the contours of the patient table.

When the imaging arrangement is not in use, i.e. in a neutral position, a part of the arrangement can be stored below a patient support, e.g. a patient table, and another part is arranged in the ceiling area above the working field around the patient table. The imaging arrangement can position the X-ray source and the detector longitudinally and laterally with respect to the patient table, or spherically around a virtual isocenter. Both parts of the arrangement are capable of freely moving the X-ray source and detector in six degrees of freedom.

Two dedicated mechatronic systems support an X-ray source and an X-ray detector. The kinematic layout of these support systems enables these components to be accurately positioned over a large range of motion, while providing minimal obstruction to clinicians or other medical equipment. By connecting the X-ray source to the floor and the detector to the ceiling, the payload of both supporting systems is coupled to the nearest part of the building structure, i.e. the so-called fixed world. Further, a large scanning range of e.g. 210° is provided while maintaining a short force path between the payload and the fixed world. Specific kinematic layouts are proposed, which further decrease the length of structural components. A lightweight and stiff mechatronic design can therefore be created, which is capable of moving the imaging equipment over a sufficiently large range, with improved alignment and motion reproducibility. This leads to better 3D image quality, and decreases the excess radiation usage needed, the radiation being transferred through the patient, to guarantee full detector coverage.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings:

FIG. 4a shows a front-end side view of another example of an imaging arrangement for X-ray imaging in a first imaging position.

FIG. 4b shows the imaging arrangement of FIG. 4a in a second imaging position.

FIG. 6 shows a perspective view of the example of FIG. 4a.

DETAILED DESCRIPTION OF EMBODIMENTS

Figure 1:
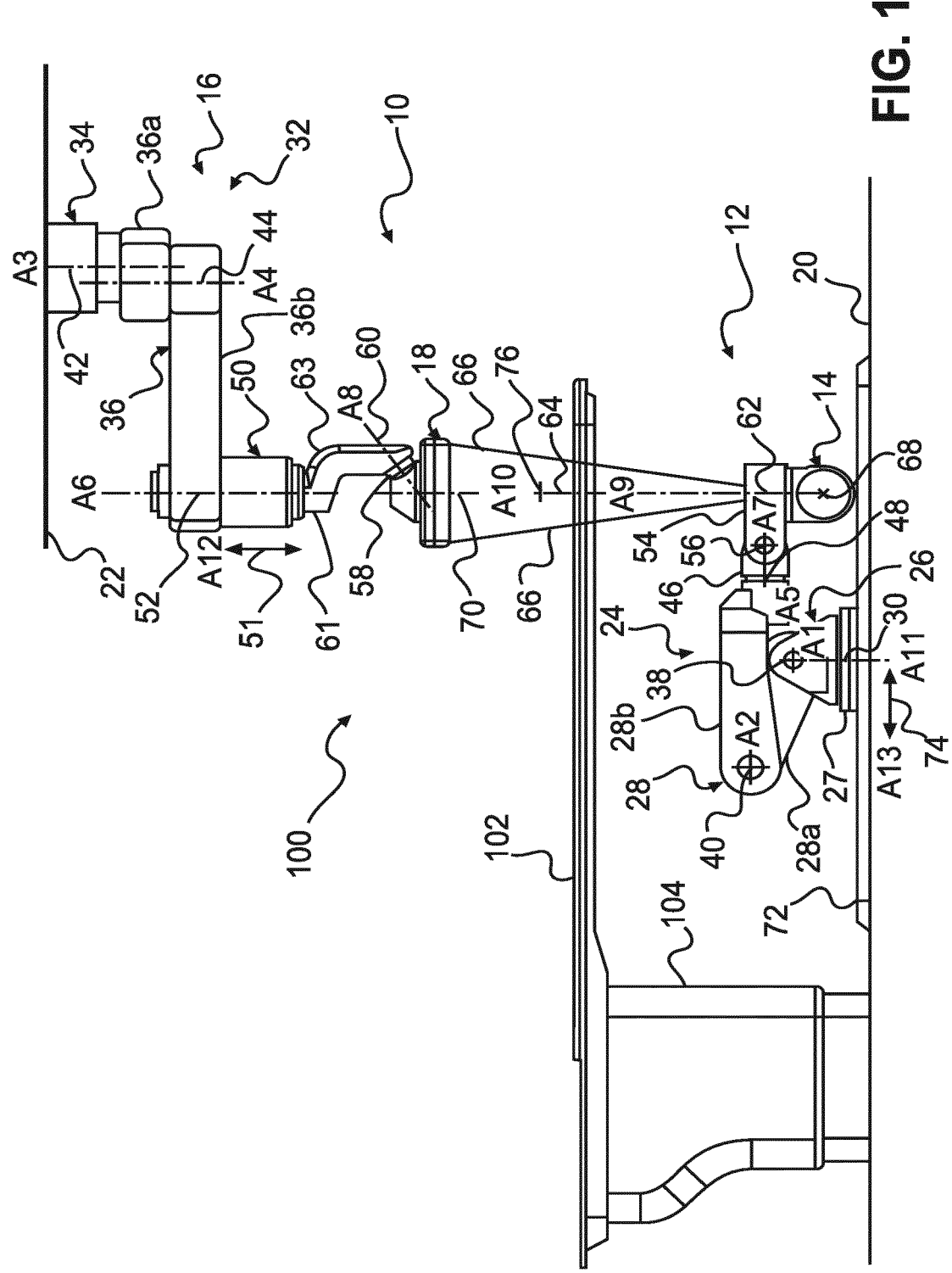
FIG. 1 shows a lateral side view of an example of an imaging arrangement for X-ray imaging. As an option, the arrangement is shown in the context of an example of an X-ray imaging system.

FIG. 1 shows a lateral side view of an example of an imaging arrangement 10 for X-ray imaging. The imaging arrangement 10 for X-ray imaging comprises a lower movable support arrangement 12 movably holding an X-ray source 14. The imaging arrangement 10 for X-ray imaging further comprises an upper movable support arrangement 16 movably holding an X-ray detector 18. The lower movable support arrangement 12 is configured to be mounted to a floor 20, and the upper movable support arrangement 16 is configured to be mounted to a ceiling 22. The lower movable support arrangement 12 comprises a lower boom 24 rotatably attached to a lower base 26. The lower boom 24 comprises two rotatably connected lower arms 28. The lower base 26 is rotatable around a vertical axis 30. The upper movable support arrangement 16 comprises an upper boom 32 rotatably attached to an upper base 34. The upper boom 32 comprises two rotatably connected upper arms 36. The rotation axes of the lower boom are arranged horizontally, and the rotation axes of the upper boom are arranged vertically.

As an option, the arrangement is shown in the context of an example of an X-ray imaging system 100. The X-ray imaging system 100 comprises an imaging arrangement 10 for X-ray imaging according to one of the preceding and following examples. Further, a subject support table 102 is provided. The lower movable support arrangement is arranged below the subject support table 102.

The subject support table 102 may comprise an adjustable stand 104, which can be lowered or raised for adjusting the table's height.

The lower movable support arrangement 12 can also be referred to as first movable support arrangement, and the upper movable support arrangement 16 can also be referred to as second movable support arrangement. The lower boom 24 can also be referred to as first boom and the upper boom 32 as second boom. The lower base 26 can also be referred to as floor-base. The lower movable support arrangement 12 can also be referred to as movable base support arrangement. The upper base 34 can also be referred to as ceiling-base. The upper movable support arrangement 16 can also be referred to as ceiling support arrangement. The booms with the two arms can also be referred to as two-arm booms. The two-arm booms can further be referred to as two-segment cantilever arms.

In an example, the upper base 34 is a fixed base.

In an example shown, the upper base 34 is mounted to a ceiling structure, like the ceiling 22, and the lower base 26 is mounted to a floor structure, like the floor 20.

The X-ray source 14 and the X-ray detector 18 can thus be arranged in many positions with respect to an object in a way that the X-ray source 14 and the X-ray detector 18 are facing each other.

A synchronized control may be provided that ensures minimal obstruction of the arrangement 10 to the user during use of the X-ray imaging system 100.

In a further example, shown as an option in FIG. 1, for the two rotatably connected lower arms 28, the lower boom comprises a first arm 28a movably attached to the lower base 26 around a first axis 38, and a second arm 28b movably attached to a free end of the first arm 28a around a second axis 40. For the two rotatably connected upper arms 36, the upper boom comprises a third arm 36a movably attached to the upper base 34 around a third axis 42, and a fourth arm 36b movably attached to a free end of the third arm 36a around a fourth axis 44.

For the rotation axes of the lower boom 24, the first axis 38 and the second axis 40 are arranged in a horizontal direction substantially parallel to each other. For example, in operation, the first axis 38 and second axis 40 maintain their horizontal arrangement, so that the arms of the lower boom 24 essentially move in the vertical plane only. In other words, movements of the arms of the lower boom 24 are restricted to the vertical plane in this example.

For the rotation axes of the upper boom 32, the third axis 42 and the fourth axis 44 are arranged in a vertical direction substantially parallel to each other. For example, in operation, the third axis 42 and fourth axis 44 maintain their vertical arrangement, so that the arms of the upper boom 32 essentially move in the horizontal plane only. In other words, movements of the arms of the upper boom 32 are restricted to the horizontal plane in this example.

It is noted that throughout the application, different orientations of axes are referred to, comprising slight deviations or a tolerance range. For example, a deviation of less than 10° is provided, e.g. less than 5° or less than 1°.

The term "substantially" parallel refers to an arrangement where a small deviation from a theoretical parallel alignment is provided. For example, a deviation of less than 10° is provided, e.g. less than 5° or less than 1°. The term "substantially parallel" can also be referred to as "essentially parallel" or "nominally parallel".

The arms are connected at their respective ends. The term "free end" refers to the distal end in view of the other end being already described as connected, which would then be the proximal end. The terms "distal" and "proximal" relate to a constructive viewing direction starting from the base towards the moving end in form of the X-ray source 14 or X-ray detector 18.

The first arm 28a of the lower boom 24 can also be referred to as first lower arm, and the second arm 28b of the lower boom 24 as second lower arm. The third arm 36a of the upper boom 32 can also be referred to as first upper arm, and the fourth arm 36b of the upper boom 32 as second upper arm.

The first axis 38 and the second axis 40 maintain in an essentially horizontal orientation throughout the use. Further, the third axis 42 and the fourth axis 44 maintain in an essentially vertical orientation throughout the use.

In a further example, shown as another option in FIG. 1, the lower movable support arrangement 12 further comprises a holding segment 46 movably attached to a free end of the second arm rotatable around a fifth axis 48 perpendicular to the first axis 38 and the second axis 40, and the X-ray source 14 is movably attached to a free end of the holding segment 46.

In an option, not further shown, the fifth axis 48 is inclined in relation to a longitudinal axis of the second arm 28b in a downward direction. For example, an inclination of approximately 45° pointing downwards is provided when the second arm 28b is arranged horizontally.

The upper movable support arrangement 16 further comprises a vertical telescopic member 50 movably attached to a free end of the fourth arm 36b rotatable around a sixth axis 52 that is substantially parallel to the third axis 42 and the fourth axis 44, and the X-ray detector 18 is movably attached to a free end of the vertical telescopic member 50. The telescopic member allows a vertical movement, as indicated with a first double arrow 51. In an example, as shown, the telescopic member 50 comprises one stage with two parts or elements moving in relation to each other; and one part or element fixed to the support.

In another example, the telescopic member 50 comprises two stages with three parts or elements moving in relation to each other; and one part or element fixed to the support.

In a further example, shown as another option in FIG. 1, the X-ray source 14 is carried by a mounting segment 54 movably mounted to the holding segment rotatable around a seventh axis 56 perpendicular to the fifth axis 48. The X-ray detector 18 is carried by a mounting member 58 movably mounted to the telescopic member rotatable around an inclined eighth axis 60. In an example, as shown, the telescopic member 50 comprises a lower part 61 that has an L-shaped end or extension 63, to which the mounting member 58 is rotatably mounted.

In an example, the eighth axis 60 is inclined in relation to the third, fourth and sixth axes. For example, provided as an option, the eighth axis 60 is inclined to the vertical direction by an angle of 52.5°.

In a further example, shown as another option in FIG. 1, the X-ray source 14 is attached to the mounting segment 54 rotatable around a ninth axis 62 that is perpendicular to the seventh axis 56. The ninth axis 62 is collinear to a centerline 64 of an X-ray bundle direction of the X-ray source 14, i.e. of an X-ray beam indicated with its outlines 66. The centerline can also be referred to as main radiation direction. A first offset is provided between the seventh axis 56 and the ninth axis 62 (B, see FIG. 4b). Further, a second offset is provided between the seventh axis 56 and a focal point 68 of the X-ray source 14 (A, also see FIG. 4b). It is noted that the first offset and the second offset are provided as two options that can be provided separately or together.

In a further example, shown as another option in FIG. 1, the X-ray detector 18 is attached to the mounting member 58 rotatable around a tenth axis 70 that is perpendicular to an imaging plane of the X-ray detector 18. The ninth axis 62 passes through the focal point 68, i.e. the focal spot of the X-ray source 14. The tenth axis 70 passes through the middle of an imaging plane of the detector 18.

It is noted that the passing of the ninth and tenth axes through the focal point 68 and middle of the imaging plane respectively are provided as an option.

As an option, it is provided that when the X-ray source 14 and the X-ray detector 18 are aligned, the tenth axis 70 also passes through the focal point 68, but not when the system is in parking position.

In another option, a virtual intersection point of the sixth axis 52, the eighth axis 60 and the tenth axis 70 is provided. An offset (C, see FIG. 4b.) is provided between the intersection point and a connection of the mounting member to the telescopic member. In an example, the intersection point is arranged in an image plane of the X-ray detector.

In a further example, shown as another option in FIG. 1, the lower base 26 is mounted to the floor 20 rotatable around the vertical axis 30 and the lower base 26 is movably mounted slidable along a floor rail 72. The floor rail 72 allows movement, indicated by a second double arrow 74, along a length of the patient table 102. The vertical rotation axis of the lower base is also referred to as eleventh axis.

It is noted that even though the floor rail 72 is shown throughout FIGS. 1 to 9, the floor rail is provided as an option. Examples are also provided, in which the lower base is mounted to the floor without a rail.

In a further example, not shown in detail, a two-part base is provided that has a first part mounted to the floor and a second part mounted to the first part in a horizontally sliding manner. The lower boom is rotatably attached to the second part. The shifting between the first and the second part of the base allows a certain adjustment in horizontal direction.

The vertical movement 51 of the telescopic member 50 provides a further line of motion, i.e. a translational movement. This can be referred to as twelfth line or axis of motion.

In an example, the lower base 26 is mounted to a carriage 27 (not shown in detail) that is slidable along the floor rail 72. The sliding movement 74 along the rail 72 provides a further line of motion, i.e. a translational movement. This can be referred to as thirteenth line or axis of motion.

The extra degree of freedom provided by the floor rail offers a redundancy in freedom of motion.

In case of a rail on which the lower base is mounted, the rail is aligned, or at least parallel to the longitudinal axis of the subject support.

The first axis 38 is also referred to as $A_1$, the second axis 40 as $A_2$, the third axis 42 as $A_3$, the fourth axis 44 as $A_4$, the fifth axis 48 as $A_5$, the sixth axis 52 as $A_6$, the seventh axis 56 as $A_7$, the eighth axis 60 as $A_8$, the ninth axis 62 as $A_9$, the tenth axis 70 as $A_{10}$, the eleventh axis 30 as $A_{11}$, the twelfth line or axis of motion 51 as $A_{12}$ and the thirteenth line or axis of motion 74 as $A_{13}$.

Figure 2:
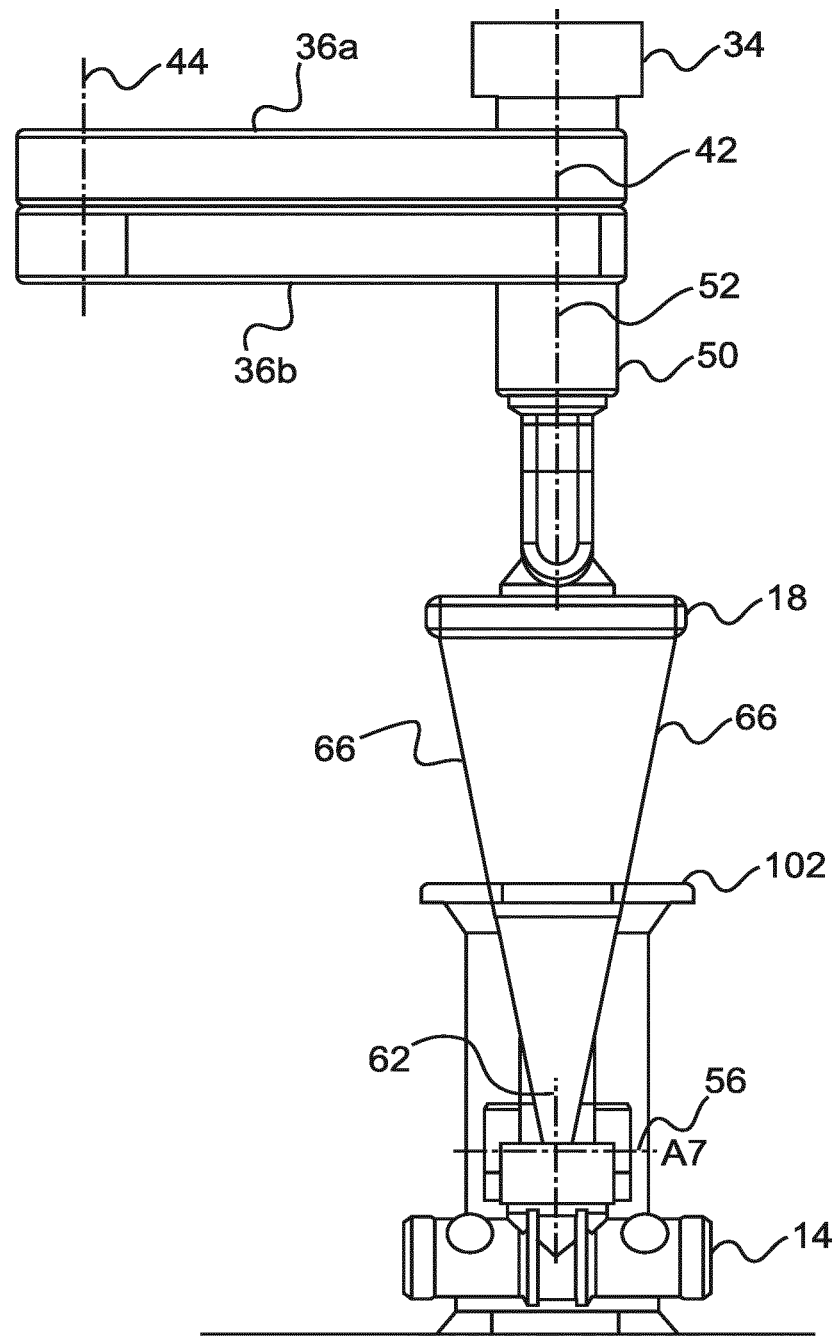
FIG. 2 shows a front-end side view of the example of FIG. 1.

FIG. 2 shows a front-end side view of the subject support table 102. The X-ray source 14 is arranged below the table and the X-ray radiation 66 is radiated towards the detector 18. The space besides the table is not obstructed by the imaging arrangement.

Figure 3:
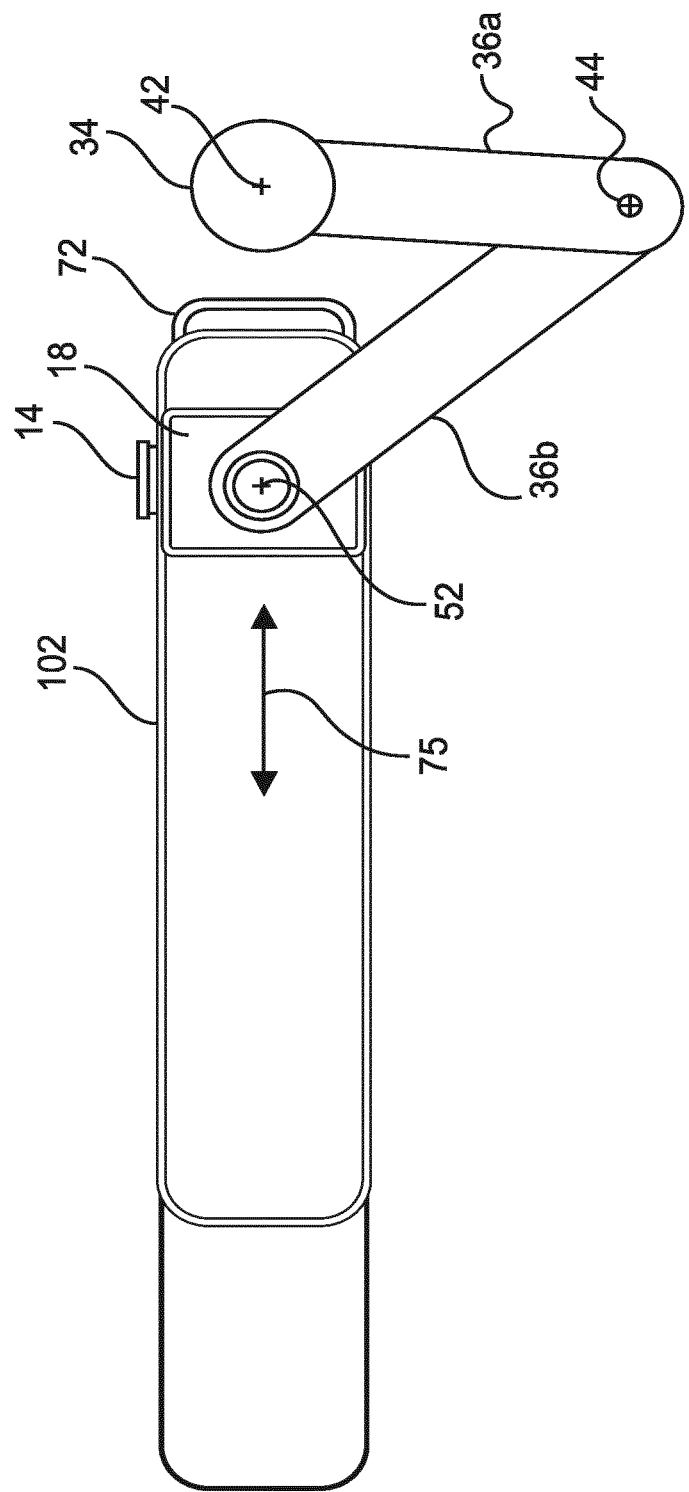
FIG. 3 shows a top view of the example of FIG. 1 and FIG. 2.

FIG. 3 shows a top view of the example of FIGS. 1 and 2. The X-ray detector 18 is arranged above the subject support table 102, and the X-ray source 14 below the subject support table 102. In addition to the movability of the lower base 26 of the lower movable support arrangement 12 in the length direction of the subject support table 102 (see arrow 74 in FIG. 1), also the X-ray detector 18 as a part of the upper movable support arrangement 16 can be moved over a large range of motion, such as the length direction of the subject support table 102, as indicated with a double arrow 75.

FIG. 4a shows a front-end side view of another example of the imaging arrangement 10 for X-ray imaging in a first imaging position. The lower movable support arrangement 12 provides a mechatronic support system for the X-ray source 14. The upper movable support arrangement 16 provides a mechatronic support system for the X-ray detector 18. The two mechatronic support systems are used to position the X-ray source 14 and the X-ray detector 18 longitudinally and laterally with respect to the patient table 102, or spherically around a virtual isocenter 76, as indicated in FIG. 4a and FIG. 4b. Both mechatronic support systems are capable of freely moving the X-ray source 14 and the X-ray detector 18 in six degrees of freedom.

FIG. 4b shows the imaging arrangement 10 of FIG. 4a in a second imaging position. In the lower part, the six degrees of freedom can be combined with the linear movement along the rail to move the X-ray source 14 spherically around the virtual isocenter 76. Oblique projections up to ±105° can be achieved. This allows e.g. for a 210° 3D scan range, which is sufficient for the use of exact reconstruction algorithms.

In an example, the length of the first arm 28a and the second arm 28b can be chosen arbitrarily.

In an option, the second arm 28b is longer than the first arm 28. This makes it easier to keep the joint between the first 28a and second arm 28b beneath the subject support table 102 during movements. The combined length is chosen such that it allows for the ±105° scan range, without fully stretching the arm (avoiding a singular point in the kinematics, which would result in difficulties adjusting the motion velocity). Furthermore, it ensures a clearance between this joint and the patient table for all positions of the first arm 28a. In FIG. 4a, the clearance is indicated with TC. This clearance enables the patient table to be adjusted to an ergonomic working height e.g. in a range of 100 mm.

The six degrees of freedom motion capability of both the top and bottom system can then also be used to vary the height of the virtual isocenter 76 accordingly.

In the top system, the rotation of the third and fourth arms 36a, 36b, and the vertical telescopic member 50, around axes 42, 44, and 52 allows for the detector 18 to be moved in a horizontal plane over three degrees of freedom. The telescopic member enables the vertical movement of the detector 18. In this embodiment, the sixth axis 52 and the vertical movement 51 are collinear.

All these factors combined ensure that the components of the top system move either above head height (2.10 m), or directly above the detector (see FIG. 2). This again limits obstruction of the imaging arrangement to the clinicians or other medical equipment.

In an example, shown in FIG. 4b, the X-ray source 14 is mounted with certain offsets (A, B). These offsets reduce the length of the first and second arm that is required to achieve the ±105° scan range. Furthermore, in the top system, the sixth axis, the eighth axis and the tenth axis intersect in a single point 77. This creates a spherical motion stage. Together with the mounting offset (C), it reduces the required stroke of the telescopic member 50.

The redundant kinematic layout (seven degrees of freedom in total) of the lower system, provided as an option, enables system movements to be programmed such that the lower boom operates within the width of the subject support table 102, for all projection angles and 3D scan trajectories (FIG. 4a and FIG. 4b). This causes only the part that connects to the X-ray source 14 to protrude from under the patient table. Furthermore, the X-ray source 14 can be held in a constant orientation with respect to the patient's longitudinal axis and the detector 18. This further limits obstruction, and minimizes visibility of the source's heel effect.

Figure 5:
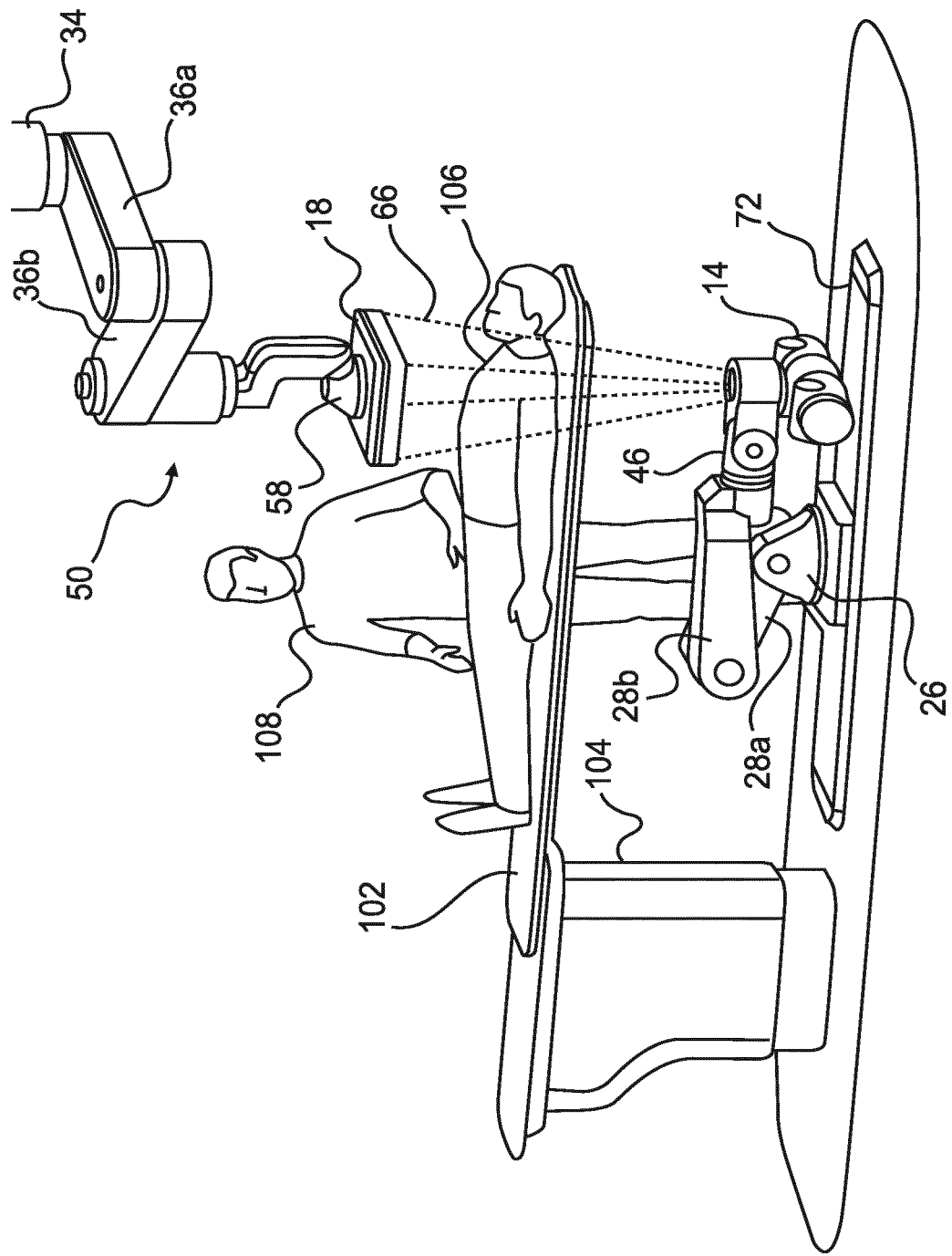
FIG. 5 shows a perspective view of the example of FIG. 1 in an imaging position.

FIG. 5 shows a perspective view of the example of FIG. 1. In an example, as indicated for example in FIG. 5, the lower boom 28 remains below the subject support table 102 when the X-ray source 14 is arranged below the subject support table 102. A subject 106 is shown resting on the subject support table 102. Further, a staff member 108, e.g. a surgeon, is shown standing next to the subject support table 102. As indicated in FIG. 5, the kinematic layout enables an ergonomic working posture, easy parking (see FIG. 7), improved patient access, and provides minimal obstruction to the clinicians, or other medical equipment. In another example, the upper movable support arrangement 16 is arranged with its upper base 34 displaced longitudinally and/or sidewardly with respect to the subject support table 102. The displacement results in that the (upper) base is not above the patient table and is thus outside a laminar air flow field.

Figure 6:
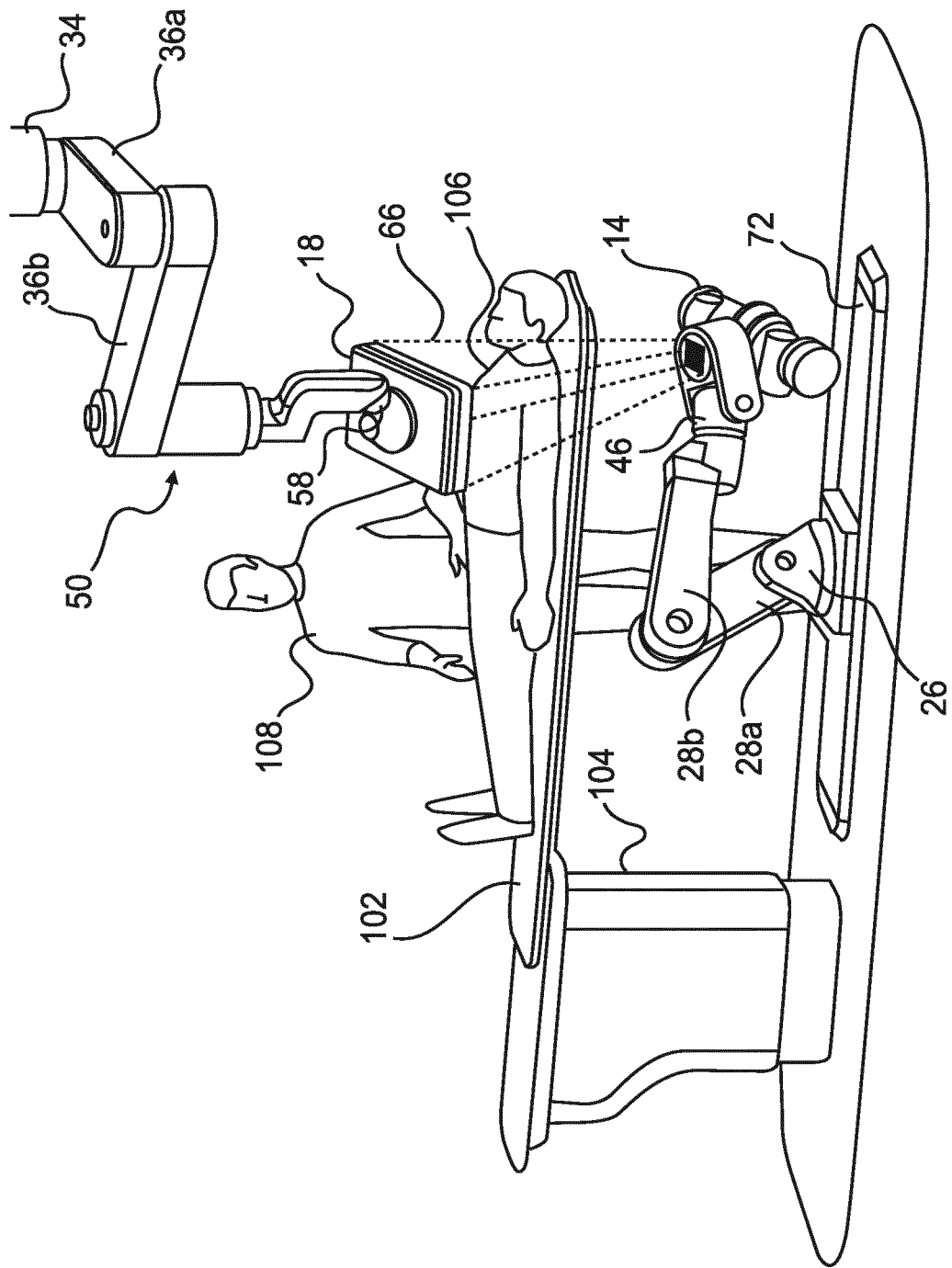

FIG. 6 shows a perspective view of the example of FIG. 4a.

Reducing the link lengths and telescopic stroke results in smaller forces and torques due to gravitational and inertial loads. It therefore allows for the arrangement to be more lightweight, and contributes to a stiffer design. The resulting higher stiffness to mass ratio will lead to improved dynamic motion performance, and thus increased image quality. The improved motion performance, combined with the six degrees of freedom motion capability, also enables active control of the alignment between the imaging equipment. Quasi-static deflections in the mechanical structure can be quantified, and compensated for, using the system's degrees of freedom. Misalignment of the X-ray beam on the detector, and therefore an unnecessary radiation dose, can hereby be minimized. Apart from improved performance, a lower system mass will also result in reduced cost of production, transport, and installation.

If the device is (temporarily) not needed, its flexible setup enables it to be parked easily. Hereto, the bottom system folds to its neutral position beneath the patient table. For the top system, the arms can be used to move the detector, telescopic member and arms away from the patient table.

Figure 7:
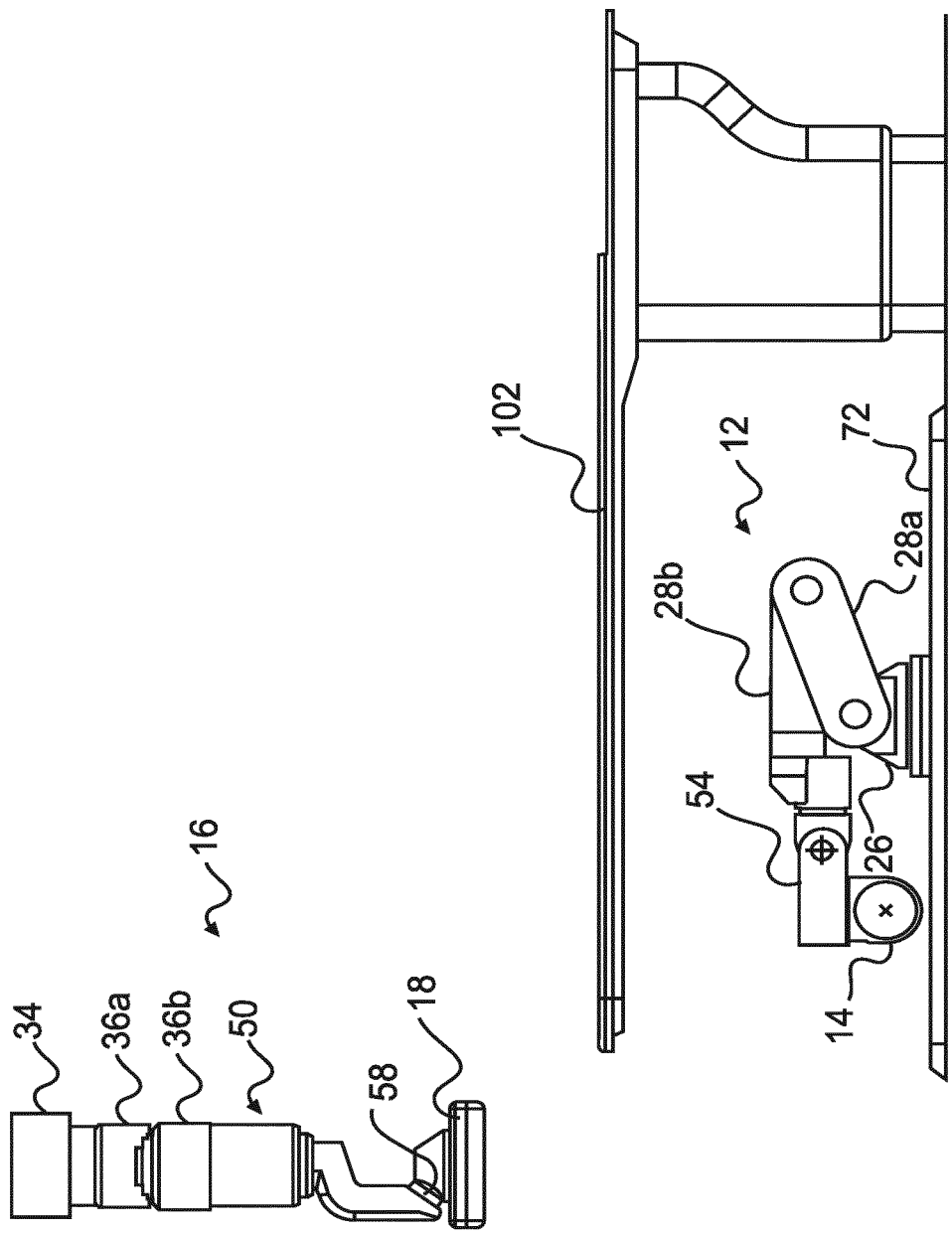
FIG. 7 shows a lateral side view of the imaging arrangement in a parking position.

FIG. 7 shows a lateral side view of the imaging arrangement 10 in a parking position. In an example, as indicated for example in FIG. 7, the upper movable support arrangement 14 is arranged with its upper base 34 displaced longitudinally above the subject support table 102. Thus, a sterile laminar downflow can be arranged that covers the subject support table 102, and the upper base 34 is arranged outside the laminar downflow. For example, the upper base 34 is placed in an extension of the table's length direction. As an option, a sideward displacement may also be provided, i.e. a displacement in the direction of the width of the table.

Figure 8:
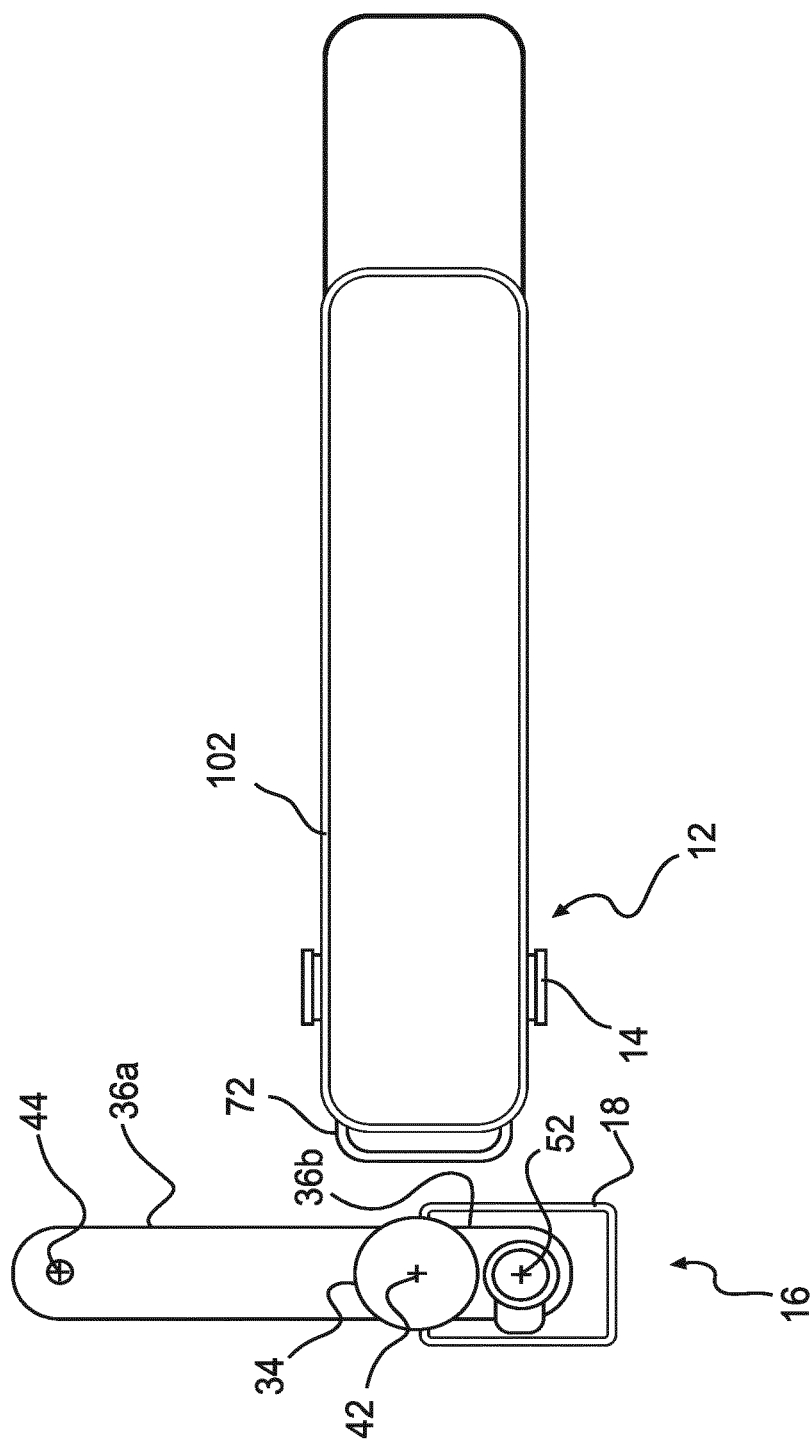
FIG. 8 shows the imaging arrangement of FIG. 7 in a top view.

FIG. 8 shows the imaging arrangement 10 of FIG. 7 in a top view. The upper movable support arrangement 16 with the X-ray detector 18 is located besides the subject support table 102 (when vertically projected). The lower movable support arrangement 12 with the X-ray source 14 is arranged below the subject support table 102.

As an option, the fourth arm 36b is longer than the third arm 36a. This allows the telescopic member 50 and attached components to be moved away from the table, alongside the base 34, despite parts of the telescopic member protruding above the fourth arm 36b.

Figure 9:
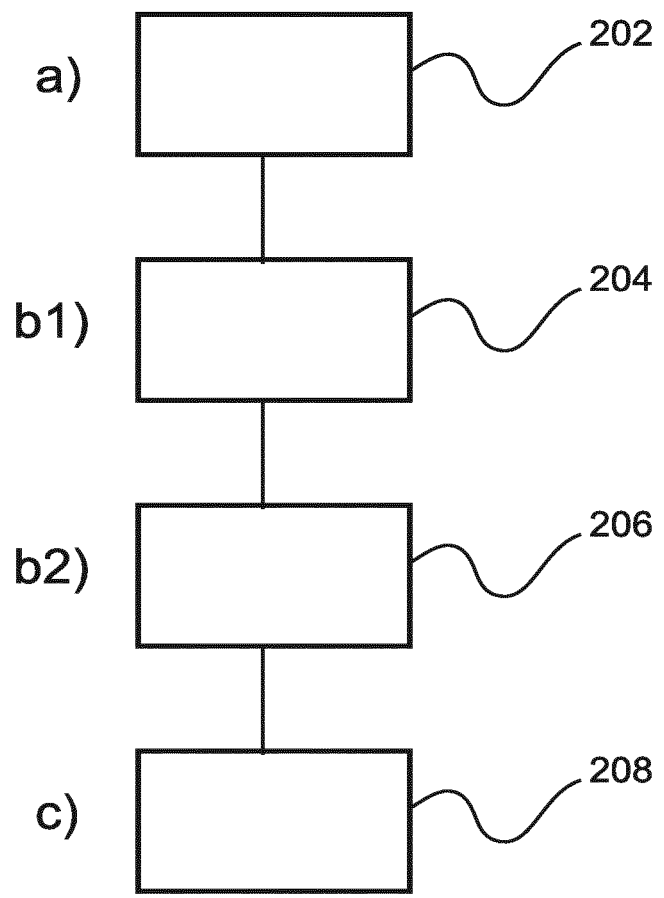
FIG. 9 shows basic steps of an example of a method for moving an imaging arrangement for X-ray imaging.

FIG. 9 shows basic steps of an example of a method 200 for moving an imaging arrangement for X-ray imaging. The method 200 comprises the following steps:

In a first step 202, also referred to as step a), a subject is provided on a subject support table.

In a second step 204, also referred to as step b1), an X-ray source is positioned using a lower movable support arrangement mounted to a floor below the subject support table. A lower boom comprises two rotatably connected lower arms that are rotating in a vertical plane about corresponding rotation axes being arranged horizontally. The lower boom may be attached to a lower base mounted to the floor, which lower base is rotatable around a vertical axis.

In a third step 206, also referred to as step b2), an X-ray detector is positioned using an upper movable support arrangement mounted to a ceiling. An upper boom comprises two rotatably connected upper arms that are rotating in a horizontal plane about corresponding rotation axes being arranged vertically. The upper boom may be attached to an upper base mounted to the ceiling, which upper base may be rotatable around a further vertical axes. Still further, at the free end of one of the rotating arms, for example the free end of the rotating arm having the greatest distance to the upper base, a telescopic member is movably attached so as to move the X-ray detector vertically, i.e. perform height adjustments of the X-ray detector.

In a fourth step 208, also referred to as step c), X-ray radiation is generated with the X-ray source and the generated X-ray radiation is detected with the X-ray detector. It is noted that in an option, the second step, the third step and the fourth step are executed synchronously.

The arrangement allows for the imaging equipment to be moved over a large range of motion. Its kinematic layout enables an ergonomic working posture, easy parking, improved patient access, and provides minimal obstruction to the clinicians, or other medical equipment.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An imaging arrangement for X-ray imaging, comprising:
    a lower movable support arrangement movably holding an X-ray source; and
    an upper movable support arrangement movably holding an X-ray detector;
    wherein the lower movable support arrangement is configured to be mounted to a floor, and the upper movable support arrangement is configured to be mounted to a ceiling;
    wherein the lower movable support arrangement comprises a lower boom rotatably attached to a lower base; wherein the lower boom comprises two rotatably connected lower arms configured to move in a vertical plane about corresponding rotation axes being arranged horizontally, the two rotatably connected lower arms comprising a first arm and a second arm;
    wherein the lower base is rotatable around a vertical axis;
    wherein the upper movable support arrangement comprises an upper boom rotatably attached to an upper base, the upper boom comprising two rotatably connected upper arms configured to move in a horizontal plane about corresponding rotation axes being arranged vertically, the two rotatably connected upper arms comprising a third arm and a fourth arm, and
    wherein the upper movable support arrangement further comprises a telescopic member movably attached to a free end of the fourth arm rotatable around an axis arranged in a vertical direction, the telescopic member configured to allow vertical movements of the X-ray detector that is movably attached to a free end of the telescopic member.

2. The imaging arrangement according to claim 1,
    wherein the first arm is movably attached to the lower base around a first axis, and the second arm is movably attached to a free end of the first arm around a second axis;
    wherein the third arm is attached to the upper base around a third axis, and the fourth arm is movably attached to the free end of the third arm around a fourth axis; and
    wherein, for the rotation axes of the lower boom, the first axis, and the second axis are arranged in a horizontal direction substantially parallel to each other; and, for the rotation axes of the upper boom, the third axis and the fourth axis are arranged in the vertical direction substantially parallel to each other.

3. The imaging arrangement according to claim 2,
    wherein the lower movable support arrangement further comprises a holding segment movably attached to a free end of the second arm rotatable around a fifth axis perpendicular to the first and second axes, and the X-ray source is movably attached to a free end of the holding segment;
    wherein the vertical telescopic member of the upper movable support arrangement is movably attached to the free end of the fourth arm rotatable around a sixth axis which is essentially parallel to the third and fourth axes.

4. The imaging arrangement according to claim 3, wherein the fifth axis is inclined in relation to a longitudinal axis of the second arm in a downward direction.

5. The imaging arrangement according to claim 3,
    wherein the X-ray source is carried by a mounting segment movably mounted to the holding segment rotatable around a seventh axis perpendicular to the fifth axis; and
    wherein the X-ray detector is carried by a mounting member movably mounted to the telescopic member rotatable around an inclined eighth axis.

6. The imaging arrangement according to claim 5, wherein the eighth axis is inclined in relation to the third, fourth and sixth axes;

wherein the eighth axis is inclined to the vertical direction by 52.5°.

7. The imaging arrangement according to claim 5, wherein at least one of:
the X-ray source is attached to the mounting segment rotatable around a ninth axis that is perpendicular to the seventh axis;
the ninth axis is collinear to a centerline of an X-ray bundle direction of the X-ray source; and/or
a first offset is provided between the seventh axis and the ninth axis;
a second offset is provided between the seventh axis and a focal point of the X-ray source.

8. The imaging arrangement according to claim 5, wherein the X-ray detector is attached to the mounting member rotatable around a tenth axis that is perpendicular to an imaging plane of the X-ray detector;
wherein a ninth axis passes through a focal spot of the X-ray source; and
wherein the tenth axis passes through a middle of an imaging plane of the detector.

9. The imaging arrangement according to claim 8, wherein a virtual intersection point of the sixth axis, the eighth axis and the tenth axis is provided; and
wherein an offset is provided between the intersection point and a connection of the mounting member to the telescopic member.

10. The imaging arrangement according to claim 2, wherein at least one of:
the second arm is longer than the first arm; or
the fourth arm is longer than the third arm.

11. The imaging arrangement according to claim 1, wherein the lower base is mounted to the floor rotatable around a vertical axis;
wherein, the lower base is movably mounted slidable along a floor rail;
wherein the floor rail allows movement along a length of a patient table; and
wherein a redundant kinematic layout of seven degrees of freedom in total of the lower system is provided that enables system movements to be programmed such that the lower boom operates within the width of the subject support table.

12. An X-ray imaging system, comprising:
the imaging arrangement for X-ray imaging according to claim 1; and
a subject support table;
wherein the lower movable support arrangement is arranged below the subject support table.

13. The X-ray imaging system according to claim 12, wherein the lower boom remains below the subject support table when the X-ray source is arranged below the subject support table.

14. The X-ray imaging system according to claim 12, wherein the upper movable support arrangement is arranged with its upper base displaced at least one of longitudinally or sidewardly in relation to the subject support table when projected downwardly.

15. A method for acquiring X-ray images of a subject, the method comprising:
providing a subject on a subject support table;
positioning an X-ray source with a lower movable support arrangement mounted to a floor below the subject support table, wherein positioning the X-ray source comprises; i) moving two rotatably connected lower arms of a lower boom in a vertical plane about corresponding rotation axes being arranged horizontally, the two rotatably connected lower arms comprising a first arm and a second arm and ii) rotating a lower base to which the lower arms are attached around a vertical axis;
positioning an X-ray detector with an upper movable support arrangement mounted to a ceiling, wherein positioning the X-ray detector comprises i) moving two rotatably connected upper arms of an upper boom in a horizontal plane about corresponding rotation axes being arranged vertically, the two rotatably connected upper arms comprising a third arm and a fourth arm and ii) moving the X-ray detector vertically by means of a telescopic member that is movably attached to a free end of the fourth arm rotatable around an axis arranged in a vertical direction, wherein the X-ray detector is movably attached to a free end of the telescopic member; and
generating X-ray radiation with the X-ray source and detecting the generated X-ray radiation with the X-ray detector.

16. The method according to claim 15,
wherein the first arm is movably attached to the lower base around a first axis, and the second arm is movably attached to a free end of the first arm around a second axis;
wherein the third arm is attached to an upper base around a third axis, and the fourth arm is movably attached to the free end of the third arm around a fourth axis; and
wherein, for the rotation axes of the lower boom, the first axis and the second axis are arranged in a horizontal direction substantially parallel to each other; and, for the rotation axes of the upper boom, the third axis and the fourth axis are arranged in the vertical direction substantially parallel to each other.

17. The method according to claim 16,
wherein the lower movable support arrangement further comprises a holding segment movably attached to a free end of the second arm rotatable around a fifth axis perpendicular to the first and second axes, and the X-ray source is movably attached to a free end of the holding segment;
wherein the vertical telescopic member of the upper movable support arrangement is movably attached to the free end of the fourth arm rotatable around a sixth axis which is essentially parallel to the third and fourth axes.

18. The method according to claim 17, wherein the fifth axis is inclined in relation to a longitudinal axis of the second arm in a downward direction.

19. The method according to claim 17,
wherein the X-ray source is carried by a mounting segment movably mounted to the holding segment rotatable around a seventh axis perpendicular to the fifth axis; and
wherein the X-ray detector is carried by a mounting member movably mounted to the telescopic member rotatable around an inclined eighth axis.

20. The method according to claim 19, wherein at least one of:
the X-ray source is attached to the mounting segment rotatable around a ninth axis that is perpendicular to the seventh axis;
the ninth axis is collinear to a centerline of an X-ray bundle direction of the X-ray source;
a first offset is provided between the seventh axis and the ninth axis; or a second offset is provided between the seventh axis and a focal point of the X-ray source.

* * * * *